United States Patent [19]

Burgess, Jr.

[11] 4,002,251

[45] * Jan. 11, 1977

[54] PARTICULATE MATERIAL DISTRIBUTING ASSEMBLY

[76] Inventor: Ralph D. Burgess, Jr., 2800 Pheasant Road, Excelsior, Minn. 55331

[ * ] Notice: The portion of the term of this patent subsequent to Apr. 15, 1992, has been disclaimed.

[22] Filed: Jan. 30, 1975

[21] Appl. No.: 545,471

Related U.S. Application Data

[63] Continuation-in-part of Ser. No. 439,342, Feb. 4, 1974, Pat. No. 3,877,585.

[52] U.S. Cl. .......................... 214/17 CA; 198/585
[51] Int. Cl.² ........................................ B65G 65/30
[58] Field of Search ........................... 198/36–38, 198/40, 42, 83, 86, 89, 101, 106, 110–112; 214/17 A, 17 C, 17 CA, 17 CB, 17 CC; 222/56, 64, 67; 74/218, 220

[56] References Cited

UNITED STATES PATENTS

| | | | |
|---|---|---|---|
| 859,595 | 7/1907 | Camp | 198/101 |
| 2,431,580 | 11/1947 | Orr | 74/220 |
| 3,412,877 | 11/1968 | Lee et al. | 214/17 CA |
| 3,550,752 | 12/1970 | Gregor | 198/106 |
| 3,877,585 | 4/1975 | Burgess | 198/37 |

Primary Examiner—Evon C. Blunk
Assistant Examiner—Joseph E. Valenza
Attorney, Agent, or Firm—Schroeder, Siegfried, Ryan & Vidas

[57] ABSTRACT

A material distributing assembly having a simplified and improved sensing and control means for causing the distributing mechanism to move forwardly or rearwardly, as required, and cause it to always distribute its load of such material at the forwardmost point available within the receptacle with which it is utilized, is disclosed. A rotatably mounted motor pivots about its output shaft axis when the rotary sensor driven thereby is restrained, the rotation of the motor causing an electrical circuit to a forwardly driving electromagnetic clutch to be broken and closing another circuit to a rearwardly driving electromagnetic clutch, the power for the entire drive and control mechanism being derived from the material distributing mechanism.

15 Claims, 2 Drawing Figures

PARTICULATE MATERIAL DISTRIBUTING ASSEMBLY

This application is a continuation-in-part of my prior and co-pending application, Ser. No. 439,342 entitled MATERIAL DISTRIBUTING SYSTEM FOR NON-FREE-FLOWING PRODUCTS, and filed by me on Feb. 4, 1974, now matured into U.S. Pat. No. 3,877,585, dated Apr. 15, 1975.

The above patent application is directed to a novel material conveying system for adding particulate material to a bin from which material is being removed at least periodically, in such a manner as to always add the material at the rear of the supply of material already therein. U.S. Pat. No. 3,550,752 entitled AUTOMATIC STORAGE SYSTEM, for NON-FREE FLOWING PRODUCTS, issued Dec. 29, 1970, is also directed to such a system. The invention disclosed and claimed herein constitutes an improvement over each of these systems and includes some of the structure utilized in my said co-pending application.

It is a general object of my invention to provide a novel and improved material distributing assembly of simple construction and efficient operation.

A more specific object is to provide a novel and improved material distributing system which is more simple and less expensive in construction, utilizes fewer parts, minimizes need for lubrication, and has lower maintenance costs.

These and other objects and advantages of the invention will more fully appear from the following description, made in connection with the accompanying drawings, wherein like reference characters refer to the same or similar parts throughout the several views, and in which.

Figure 1:
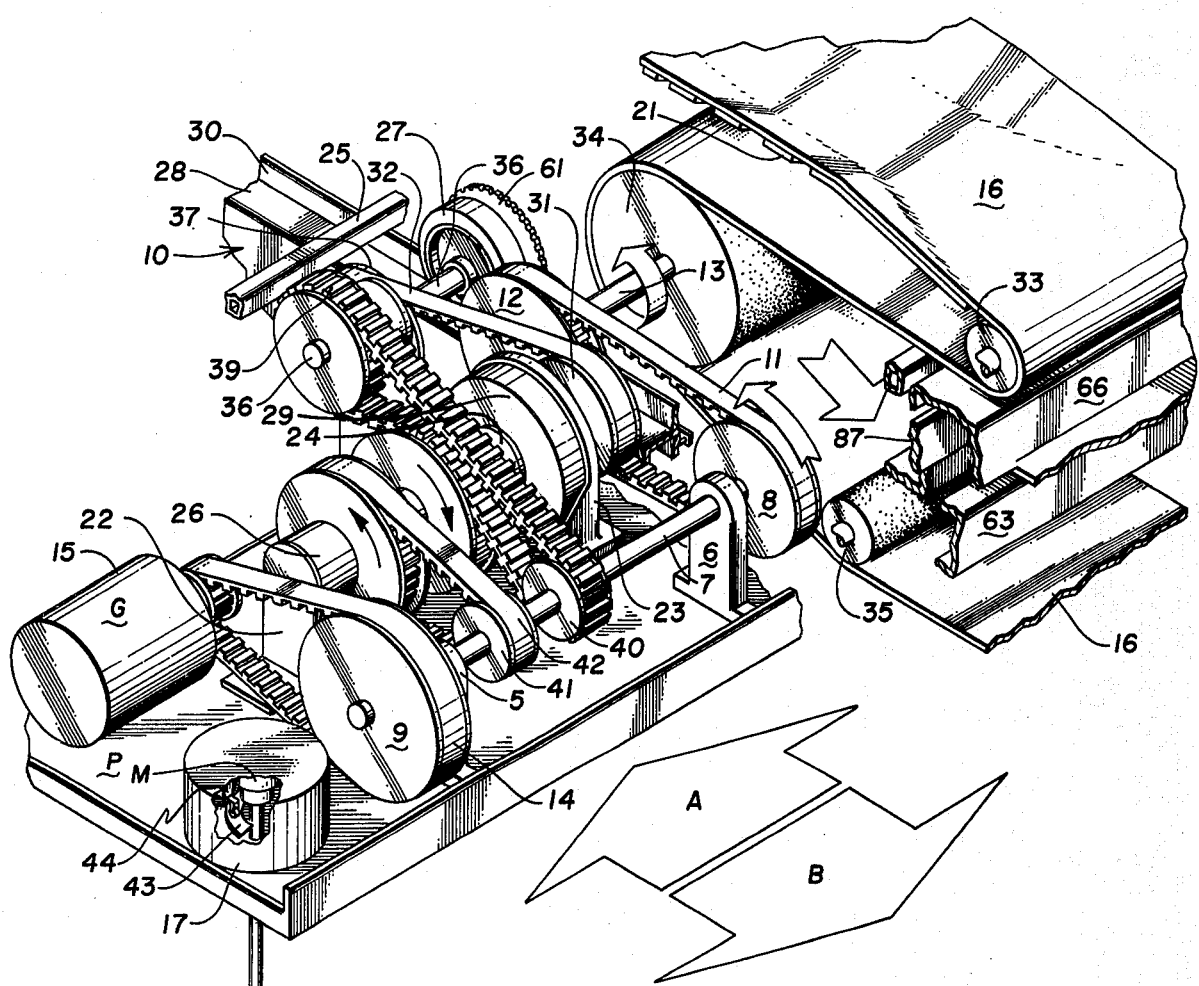
FIG. 1 is a pictorial view of the major portions of one of my material assemblies illustrating the direction of rotation of the critical parts thereof, both when the assembly is advancing and when it is retreating.

The embodiment of my invention, as shown, is designed for use in an assembly such as is shown in much greater detail in my said co-pending application and is intended to be substituted for the mechanism shown in FIG. 6 of that application. FIG. 1 of this application is patterned in layout similarly to that of said FIG. 6 although, of course, the construction and elements thereof differ. Some of the elements in the two figures are identical and the numerals applied thereto are therefore generally identical, in order to facilitate understanding of the invention. Thus, the bin 10, continuous belt 16, platform P, belt support segments 21, frame 25, rear wheels 27, track 28, guide blades 30, power take-off roller 33, belt reversing roller 34, guide roller 35, roller chain sprocket 61, subframe 63, vibrating pan 66, and counterweight 87 have all been designated by the numerals assigned thereto in my said co-pending application.

The construction shown in FIG. 1 is designed for use with the remainder of the construction shown in my said co-pending application which is included herein by reference thereto. The platform P, through bearings 5 and 6, supports shaft 7 which carries sprocket 8 at its inner end and sprocket 9 at its outer end. The sprocket 8 is driven by belt 11 and sprocket 12 which in turn is driven by power take-off shaft 13 which extends outwardly from and supports belt reversing roller 34. Shaft 13 is supported by frame 25 by a bearing (not shown) located just inwardly of sprocket 12. The direction of rotation is indicated by appropriate arrows as is the direction of movement of belt 16 from whence the power comes to drive shaft 13 as described in my said co-pending application.

Sprocket 9 drives belt 14, which in turn drives an electrical generator 15 mounted upon platform P. Generator 15 is electrically connected, as shown, in driving relation to an electric motor within clutch control 17 which is mounted upon platform P. Output shaft 18 of this motor supports rotary sensor 19 about 1 to 2 feet above the floor of bin 10 in position to engage the supply of particulate material 20 already in the bin. The clutch control 17 is of the type which is readily available on the market and can be purchased from Monitor Manufacturing, Inc., 200 North Island Avenue, Batavia, Illinois 60510, and is identified as Control Model KA, Part No. 331-111-2, 20V DC, 2 S.P. switches. If desired, their KAX Model will also function satisfactorily for these purposes.

Rotatably mounted upon platform P in juxtaposition to shaft 7 by means of bearings 22 and 23, is a shaft which carries a pair of electromagnetic clutches 24 and 26 and a reversing power reducer 29. A drive wheel 31 is connected to the gear reducer 29. A belt 32 which is driven by drive wheel 31, in turn drives shaft 36, rear wheel 27, and roller chain sprocket 61 through sprocket 37. Idler wheel 38 is carried at the outer end of shaft 36 and has double sided belt 39 entrained therearound. Drive wheel 40, which is carried by shaft 7, is also encircled by belt 39 which drives clutch 24 to move the platform P rearwardly when the clutch is engaged. Similarly, drive wheel 41 drives clutch 26 through belt 42 to drive the platform forwardly when clutch 26 is engaged.

Figure 2:
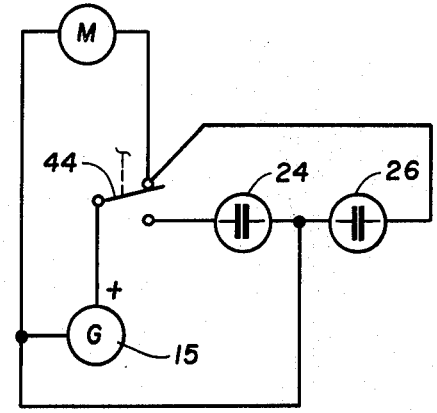
FIG. 2 is a schematic diagram of electrical circuits activated by the sensor driving motor to control the direction of movement of the assembly.
Figure 2:
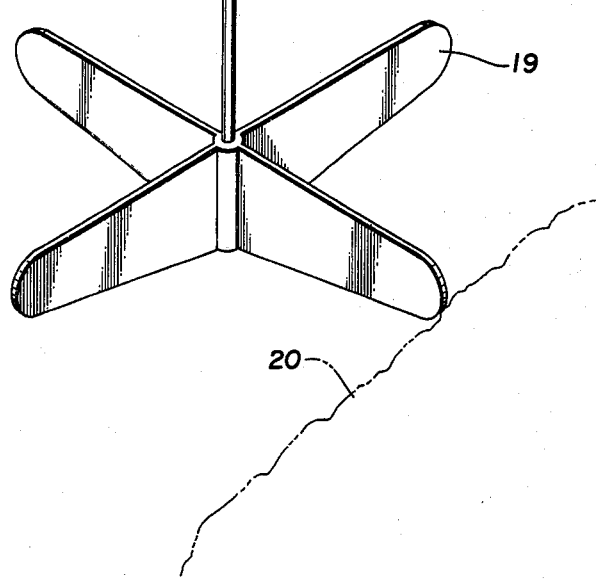

It will be noted that clutches 24 and 26 are connected electrically to generator 15 as is the motor M of control 17. The electrical connections are illustrated in FIG. 2 in which switch 44, which is normally in closed position, completes the circuit from the generator 15 through motor M as well as through forward clutch 26 so that the sensor 19 is normally driven by the motor M and the platform P with the material distributing assembly, the vibrating pan 66, of which is shown fragmentarily, is moved forwardly. When the rotating sensor 19, however, engages the particulate material 20 so that its rotation is arrested, then the motor M which is mounted for rotation about the axis of the countershaft 18 commences to rotate and rise upwardly on the ramp 43 until the switch 44 moves sufficiently to break contact with the circuit supplying current to the motor M, thereby causing the motor to stop. At the same time, the switch closes the circuit to the reversing clutch 24 which causes the latter to engage and move the platform P and the material distributing mechanism rearwardly in the direction indicated by the arrow A. Once the platform has moved sufficiently far rearwardly so that the paddles of the sensor 19 are freed, the motor which is biased in a direction opposite to that in which it has been rotated again descends the ramp and returns to its original position, thereby causing switch 44 to reestablish the circuit through the motor and again drive the sensor 19 and move the platform P forwardly.

From the above, it can be seen that this unit is self-contained in that the power is taken from the material delivering belt 16 by the power take-off shaft 13 and is delivered to the powered shaft through the belt 11. The shaft 7 drives the sprockets 40 and 41 continuously so long as the belt 16 delivers product to the vibrating pan 66. Since the switch 44 is normally closed, the electric motor M is normally in operation to drive the sensor 19. Since switch 44 is in the position shown in FIG. 2, clutch 26 is engaged and therefore, belt 42 drives sprocket 31 and belt 32 so as to cause platform P to move forwardly. When the sensor 19 engages the product 20 which is already in the bin, its rotation is arrested and motor M commences to rotate about the axis of the shaft 18 and run upwardly on the ramp 43, thereby causing switch 44 to break the circuit to the motor and establish the circuit with the clutch 24. As a consequence, shaft 7 through sprocket 40 drives sprocket 31 and belt 32 in the opposite direction, thereby causing platform P to move rearwardly until the sensor 19 becomes disengaged, at which point, motor M is again drawn down the ramp as a result of its bias until switch 44 reestablishes contact to operate motor M and clutch 26, since they are of equal impedance. Thus, the platform P and the control mechanism therefor is constantly being urged to the forwardmost location at which the particulate material should be dispensed by the vibrating pan 66 and when the material becomes sufficiently voluminous as to arrest the sensor 19, the entire assembly moves rearwardly, thereby locating the platform P and the vibrating pan 66 so that the particulate material can be properly deposited at the immediate rear of the particulate material 20 which is already in the bin. It will be noted that the effect of the belt 16 is to constantly urge the platform P forwardly. It will also be noted that the power takeoff shaft 13 drives the generator 15 through the sprocket 9 and belt 14, thereby creating a supply of electricity adequate to run the motor M and control the electromagnetic clutches 24 and 26. Thus, the entire unit is self-contained, operates automatically, and is constructed simply and at a minimum of expense since the number of parts are at a minimum.

It will, of course, be understood that various changes may be made in the form, details, arrangement and proportions of the parts without departing from the scope of the invention which consists of the matter shown and described herein and set forth in the appended claims.

What is claimed is:

1. In conveying apparatus for automatically delivering material to the forwardmost unfilled portion of a bin
   a. a movable material distributing mechanism for distributing material within a bin,
   b. powered means for delivering material to said mechanism for distribution thereby,
   c. power take-off means associated with said material delivering means and providing a source of rotary power therefrom,
   d. electrically controlled moving means driven by said source of rotary power and connected with said material distributing mechanism for automatically selectively moving the latter forwardly and rearwardly,
   e. said moving means including selective drive means connected to and powered by said source of rotary power of said power take-off means and constructed and arranged with respect to the remainder of said moving means to cause said material distributing mechanism to automatically deliver material to the forwardmost unfilled portion of the bin at all times.

2. The structure defined in claim 1 wherein said drive means includes electric clutch mechanism connected to said source of rotary power of said power take-off means and constructed and arranged to alternatively move said material distributing mechanism forwardly and rearwardly.

3. The structure defined in claim 2 and rotary sensor means carried by said material distributing mechanism and connected to said clutch mechanism in controlling relation to cause the same to alternatively so move said material distributing mechanism.

4. The structure defined in claim 3 wherein said sensor means includes a movably mounted motor driving a rotary sensor element.

5. The structure defined in claim 1 and sensor means carried by said material distributing mechanism and electrically connected to said drive means in controlling relation to cause the same to selectively cause said moving means to move said distributing mechanism in accordance with a condition sensed by said sensor means.

6. The structure defined in claim 5 wherein said sensor means includes a motor assembly having an output shaft, said assembly being mounted for movement in its entirety about said output shaft, and a rotary sensor element carried by said output shaft in sensing position and constructed and arranged to cause said motor to rotate in its entirety about the axis of said output shaft when rotation of said sensor element is restrained.

7. The structure defined in claim 3 wherein engagement and disengagement of said clutch mechanism is electrically controlled, and said rotary sensor means is comprised of a motor movably mounted on said material distributing mechanism and having an output shaft, a rotary sensor element fixedly carried by said output shaft for rotation therewith in sensing position, said motor being mounted for limited rotational movement in one direction about the axis of its output shaft when rotation of the latter is restrained by said sensor element and being biased in the opposite direction, and an electrical control circuit connected in controlling relation with said clutch mechanism and in controlled relation with said motor, said electrical control circuit being constructed and arranged with respect to said motor so as to cause said drive means to move said distributing mechanism forwardly when said motor is disposed in its furthermost position in said opposite direction and to move said distributing mechanism rearwardly when said motor is rotated to its furthermost position in said first mentioned direction against its bias.

8. The structure defined in claim 5, wherein said sensor means includes a motor powered by said power take-off means.

9. The structure defined in claim 1 wherein said material delivering means constantly urges said material distributing mechanism forwardly at all times and said drive means includes electrical clutch mechanism constructed and arranged to limit the rate of forward movement of said material distributing mechanism.

10. The structure defined in claim 8 and a generator carried by said material distributing mechanism and driven by said power take-off means and connected electrically with said motor in power-supplying relation.

11. The structure defined in claim 2, and a generator carried by said material distributing mechanism and connected in driven relation to said power take-off means and connected electrically in power-supplying relation with said clutch mechanism.

12. In conveying apparatus for automatically delivering material to the forwardmost unfilled portion of a bin
   a. a movable material distributing mechanism for distributing material within a bin,
   b. means for delivering material to said mechanism for distribution thereby,
   c. electrical clutch driven moving means for selectively moving said material distributing mechanism forwardly and rearwardly, said moving means being connected with said material delivery means in motivated relation, and
   d. sensor means carried by said distributing mechanism and connected to said moving means in controlling relation to cause the same to move said distributing mechanism forwardly or rearwardly in accordance with a condition sensed by said sensor means whereby said distributing mechanism may be caused to move rearwardly when said sensor means engages the material at the forwardmost unfilled portion of the bin and then forwardly again upon disengagement of such material by said sensor means.

13. In conveying apparatus for automatically delivering material to the forwardmost unfilled portion of a bin,
   a. a movable material distributing mechanism for distributing material within a bin,
   b. means for delivering material to said mechanism for distribution thereby,
   c. means for selectively moving said material distributing mechanism forwardly and rearwardly, said moving means being connected with said material delivery means in powered relation, and
   d. rotary sensor means carried by said distributing mechanism and electrically connected to said moving means in controlling relation to cause the same to move said distributing mechanism forwardly or rearwardly in accordance with a condition sensed by said sensor means whereby said distributing mechanism may be caused to move rearwardly when said sensor means engages the material at the forwardmost unfilled portion of the bin and then forwardly again upon disengagement of such material by said sensor means.

14. In conveying apparatus for automatically delivering material to the forwardmost unfilled portion of a bin
   a. a movable material distributing mechanism for distributing material within a bin,
   b. means for delivering material to said mechanism for distribution thereby,
   c. rotary drive means powered by said material delivering means and connected to said material distributing mechanism in selective driving relation to cause the same to move forwardly and rearwardly, and
   d. sensor means carried by said material distributing mechanism and electrically connected to said rotary drive means in controlling relation to selectively cause said rotary drive means to so move said distributing mechanism in accordance with conditions sensed by said sensor means whereby said distributing mechanism may be caused to move rearwardly when said sensor means engages the material at the forwardmost unfilled portion of the bin and then forwardly again upon disengagement of such material by said sensor means.

15. In conveying apparatus for automatically delivering material to the forwardmost unfilled portion of a bin,
   a. a movable platform capable of delivering material within a bin,
   b. means connected with said platform and urging the same in a predetermined direction,
   c. means for selectively moving said platform forwardly and rearwardly, said moving means being connected in powered relation with said platform urging means, and
   d. sensor means carried by said platform and electrically connected to said moving means in controlling relation and causing the same to move said platform forwardly and rearwardly in accordance with a condition sensed by said sensor means whereby said distributing mechanism may be caused to move rearwardly when said sensor means engages the material at the forwardmost unfilled portion of the bin and then forwardly again upon disengagement of such material by said sensor means.

* * * * *